United States Patent
Sheng et al.

(10) Patent No.: US 12,121,604 B2
(45) Date of Patent: *Oct. 22, 2024

(54) COMPOSITION COMPRISING HYDROXYLATED DIPHENYLMETHANE DERIVATIVES

(71) Applicant: L'OREAL, Paris (FR)

(72) Inventors: Le Sheng, Shanghai (CN); Xiuxia Wang, Shanghai (CN)

(73) Assignee: L'OREAL, Paris (FR)

( * ) Notice: Subject to any disclaimer, the term of this patent is extended or adjusted under 35 U.S.C. 154(b) by 289 days.

This patent is subject to a terminal disclaimer.

(21) Appl. No.: 15/768,991

(22) PCT Filed: Dec. 10, 2015

(86) PCT No.: PCT/CN2015/096986
§ 371 (c)(1),
(2) Date: Apr. 17, 2018

(87) PCT Pub. No.: WO2017/096583
PCT Pub. Date: Jun. 15, 2017

(65) Prior Publication Data
US 2018/0263875 A1 Sep. 20, 2018

(51) Int. Cl.
| | | |
|---|---|---|
| *A61K 8/34* | (2006.01) | |
| *A61K 8/06* | (2006.01) | |
| *A61K 8/42* | (2006.01) | |
| *A61K 8/81* | (2006.01) | |
| *A61Q 19/00* | (2006.01) | |

(52) U.S. Cl.
CPC ............. *A61K 8/347* (2013.01); *A61K 8/42* (2013.01); *A61K 8/8152* (2013.01); *A61Q 19/00* (2013.01); *A61K 8/062* (2013.01)

(58) Field of Classification Search
CPC ........ A61K 8/247; A61K 8/42; A61K 4/8152; A61K 8/062; A61Q 19/00; A61Q 1/00; A61Q 5/00
See application file for complete search history.

(56) References Cited

U.S. PATENT DOCUMENTS

| | | | |
|---|---|---|---|
| 6,033,647 A | 3/2000 | Touzan et al. | |
| 8,758,783 B1 * | 6/2014 | Perruna .................. | A61Q 1/02 424/401 |
| 2007/0098655 A1 | 5/2007 | Schmaus et al. | |
| 2007/0248633 A1 | 10/2007 | Baldo | |
| 2011/0052512 A1* | 3/2011 | Monello ................... | A61K 8/86 424/59 |

FOREIGN PATENT DOCUMENTS

| | | |
|---|---|---|
| CN | 1798550 A | 7/2006 |
| CN | 101084862 A | 12/2007 |
| EP | 1 847 247 A1 | 10/2007 |
| FR | 2 900 046 A1 | 10/2007 |
| JP | 10-114619 A | 5/1998 |
| JP | 2007-291102 A | 11/2007 |
| JP | 2009-522338 A | 6/2009 |
| JP | 2011-219424 A | 11/2011 |
| WO | WO 2007/077260 A1 | 7/2007 |
| WO | WO 2012/080994 A2 | 6/2012 |

OTHER PUBLICATIONS

Karande, Pankaj, and Samir Mitragotri. "Enhancement of transdermal drug delivery via synergistic action of chemicals." Biochimica et Biophysica Acta (BBA)-Biomembranes 1788.11 (2009): 2362-2373. (Year: 2009).*
Kim, Yeu-Chun, et al. "Synergistic enhancement of skin permeability by N-lauroylsarcosine and ethanol." International journal of pharmaceutics 352.1-2 (2008): 129-138. (Year: 2008).*
Belsito, Donald V., et al. "Crosslinked Alkyl Acrylates as Used in Cosmetics." pp. 1-63. (Year: 2011).*
Lubrizol, Carbopol ETD 2020 Polymer for Personal Care Applications, TDS-187, pp. 1-2. (Year: 2002).*
Office Action issued Jun. 25, 2019 in corresponding Indian Patent Application No. 201847014712, 5 pages.
Extended European Search Report issued on Apr. 3, 2019 in Patent Application No. 15910058.5, 8 pages.
International Search Report and Written Opinion issued Sep. 20, 2016 in PCT/CN2015/096986 filed Dec. 10, 2015.
Brazilian Office Action issued Sep. 17, 2019 in Brazilian Patent Application No. 112018006611-7 (with English translation), 5 pages.
Combined Chinese Office Action and Search Report issued on Apr. 27, 2020, in Patent Application No. 201580085192.3, 12 pages (with English Translation of Category of Cited Documents).

* cited by examiner

*Primary Examiner* — Jennifer Chin

(57) ABSTRACT

A composition containing at least 75% by weight of water, relative to the total weight of the composition, hydroxylated diphenylmethane derivative(s), oil(s) containing in its structure at least one amide unit, and crosslinked copolymer(s) containing at least one unit of an unsaturated olefinic carboxylic acid and at least one unit of a ($C_{10}$-$C_{30}$)alkyl ester of unsaturated carboxylic acid.

12 Claims, No Drawings

COMPOSITION COMPRISING HYDROXYLATED DIPHENYLMETHANE DERIVATIVES

The present invention relates to a composition comprising hydroxylated diphenylmethane derivative(s). It relates more particularly to a composition comprising a high content of water, hydroxylated diphenylmethane derivative(s), specific oil(s), and specific thickening agent(s).

PRIOR ART

It is known to use active agents in cosmetic and/or dermatological compositions, for example for the purpose of caring for or treating or providing beneficial effects to the skin. However, some of these active agents have the disadvantage of being unstable in conventional cosmetic solvents and/or of easily becoming degraded, especially in contact with water, in particular because of oxidation phenomena. They thus rapidly lose their activity over time and this instability runs counter to the efficacy sought.

Hydroxylated diphenylmethane derivatives are known from application WO2004/105736 in compositions in emulsion form. These hydroxylated diphenylmethane derivatives are described in this application as tyrosinase inhibitors which can be used in particular in depigmenting compositions.

These hydroxylated diphenylmethane derivatives, because in particular of their aromatic structure and their lipophilic character, have the disadvantage of being unstable and/or weakly soluble in the conventional solvents used in cosmetics. They can in particular recrystallize. They can additionally easily become degraded by light and/or temperature, in particular because of oxidation phenomena.

They thus rapidly lose their activity over time and this instability runs counter to the efficacy sought.

Besides, compositions with high content of water, for example cosmetic water, are more and more favoured by the consumers thanks to its fresh and hydration feelings after application.

Efforts have been made by the conventional products on solubilizing and stabilizing hydroxylated diphenylmethane derivatives. However, the inventors found it difficult to deliver a stable composition containing hydroxylated diphenylmethane derivatives, with a high amount of water, in other words, cosmetic compositions with low viscosity.

Moreover, compositions in form of micro emulsions, and emulsions with micellar structures, are well known as efficient delivery system in the cosmetic filed. This been said, consumers are always seeking for even better bioavailability of the cosmetic products.

The expression "bioavailability" is understood to mean, for the purposes of the present application, molecular penetration of the active agent in question into the living layers of the skin and in particular of the epidermis. The penetrated concentration sought will be the highest possible so as to increase the amount of active agent arriving as far as the living layers of the skin.

Moreover, it is sought to avoid in the formulations the excessively large presence of oily solvents for sensory reasons: final cosmetic feel of the oily or greasy type.

There is therefore a need to have compositions, in particular cosmetic compositions, comprising hydroxylated diphenylmethane derivatives with sufficient stability over time, while having, moreover, excellent bioavailability in the skin, as well as good cosmetic properties as regards the feel after application.

SUMMARY OF THE INVENTION

The applicant found that such a need can be met by formulating a composition comprising at least one hydroxylated diphenylmethane derivative and a combination of at least one specific oil and crosslinked copolymer, in the presence of high amount of water.

More specifically, the invention relates to a composition comprising:
a) greater than or equal to 75% by weight of water, relative to the total weight of the composition;
b) at least one hydroxylated diphenylmethane derivative of the formula (I),

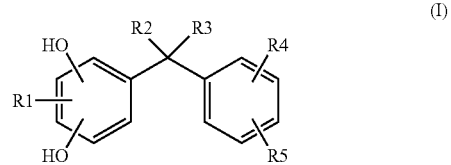

in which:
R1 is chosen from a hydrogen atom, a methyl group, a saturated or unsaturated, linear or branched alkyl chain having from 2 to 4 carbon atoms, an —OH group, and a halogen,
R2 is chosen from a hydrogen atom, a methyl group, a saturated or unsaturated linear or branched alkyl chain having from 2 to 5 carbon atoms,
R3 is chosen from a methyl group or a saturated or unsaturated linear or branched alkyl chain having from 2 to 5 carbon atoms,
R4 and R5 are, independently of each other, chosen from a hydrogen atom, a methyl group, a saturated or unsaturated linear or branched alkyl chain having from 2 to 5 carbon atoms, an —OH group or a halogen;
c) at least one oil containing in its structure at least one amide unit;
d) at least one crosslinked copolymer comprising at least one unit of an unsaturated olefinic carboxylic acid and at least one unit of a $(C_{10}\text{-}C_{30})$alkyl ester of unsaturated carboxylic acid.

The present invention also relates to a cosmetic process for caring for/making up keratin materials, in particular the skin, comprising the application to the keratin materials of the composition according to the invention.

The invention also relates to the use of the composition according to the invention for caring for keratin materials, in particular the skin.

According to the present application, "stable over time" means that the composition after two months of storage at 25 to 45° C., shows no change in appearance, colour, odour, or viscosity.

Advantageously, the composition of the present invention is a cosmetic water. By "cosmetic water", it intends to mean that the composition of the invention has a desired low viscosity, so as to provide to the skin a cosmetic properties such as a hydration and fresh feeling, instead of oily and greasy feeling.

Accordingly, the viscosity of a composition of the invention may be measured via any process known to those skilled in the art, and especially according to the following conventional process. Thus, the measurement can be carried out at 25° C. using a Rheomat 180 viscometer equipped with a spindle M2 rotating at 200 rpm.

More particularly, for the purpose of the present invention, "cosmetic water" is intended to mean a composition in form of oil in water emulsion, oil in water dispersion, aqueous solution, or micellar system containing at least 70% by weight, more preferably at least 75% by weight of water, relative to the total weight of the composition.

By "keratin materials" we intend to mean human keratin materials including the body skin, the face, the lips, the scalp, and the nails, and more specifically the face.

Other subjects and characteristics, aspects and advantages of the invention will emerge even more clearly on reading the description and the examples that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

DETAILED DESCRIPTION OF THE PREFERRED EMBODIMENTS

Hydroxylated Diphenylmethane Derivative(s)

The composition of the present invention comprises at least one hydroxylated diphenylmethane derivatives of the formula (I),

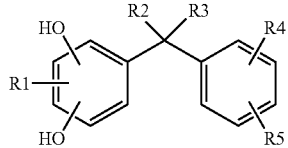

in which:
R1 is chosen from a hydrogen atom, a methyl group, a saturated or unsaturated, linear or branched alkyl chain having from 2 to 4 carbon atoms, an —OH group, and a halogen,
R2 is chosen from a hydrogen atom, a methyl group, a saturated or unsaturated linear or branched alkyl chain having from 2 to 5 carbon atoms,
R3 is chosen from a methyl group or a saturated or unsaturated linear or branched alkyl chain having from 2 to 5 carbon atoms,
R4 and R5 are, independently of each other, chosen from a hydrogen atom, a methyl group, a saturated or unsaturated linear or branched alkyl chain having from 2 to 5 carbon atoms, an —OH group or a halogen.

The —OH, R1, R4 and R5 groups may be at the ortho, meta or para position with respect to the bond formed with the carbon linking the two aromatic rings to each other.

Also included in the compounds of the invention possessing substituted phenyl groups and for which R2 and R3 are different are the enantiomeric forms of S configuration, the enantiomers of R configuration and their racemic mixture.

According to a preferred embodiment of the invention, a compound of formula (I) is used in which:

R1, R2, R4 and R5 denote a hydrogen atom; R3 is a methyl group;
the —OH groups are at the ortho and para positions with respect to the bond formed with the carbon linking the two aromatic rings to each other.

This compound corresponds to the following formula (II)

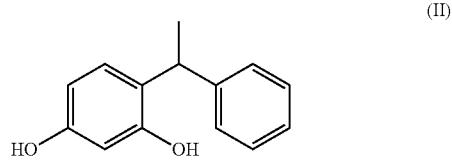 [SMILES: CC(c1ccccc1)c1ccc(O)cc1O]

called 4-(1-phenylethyl)-1,3-benzenediol or 4-(1-phenylethyl)-1,3-dihydroxybenzene or otherwise called phenylethylresorcinol or phenylethylbenzenediol or styrylresorcinol. This compound has a CAS number 85-27-8.

Such a compound is marketed under the name SYMWHITE 377® or BIO 377 by the company SYMRISE.

In particular, the composition according to the invention comprises (a) at least one hydroxylated diphenylmethane derivative of formula (II).

According to a preferred embodiment, the hydroxylated diphenylmethane derivatives of formula (I) is present in amount from 0.005% to 5% by weight, preferably from 0.01% to 3% by weight, more preferably from 0.1% to 2% by weight, relative to the total weight of the composition.

Oil(s)

The composition of the present invention comprises at least one oil containing in its structure at least one amide unit.

The expression "oil containing in its structure at least one amide unit" will be understood throughout the text of the description to mean any compound comprising in its chemical structure at least one amide group (or function) of the type:

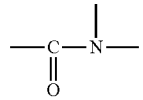

and simultaneously having the following characteristics:
a) liquid at 25° C.,
b) insoluble or immiscible in water at 25° C.,
c) no emulsifying properties.

The oil(s) having in their structure at least one amide unit in accordance with the invention is (are) preferably chosen from the compounds of formula (III) below:

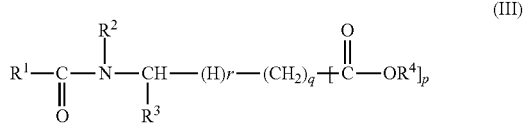

in which:
the radical $R^1$ represents an optionally functionalized, aliphatic, cycloaliphatic or cyclic, saturated or unsaturated monovalent hydrocarbon-based radical containing from 1 to 30 carbon atoms and preferably from 1 to 22 carbon atoms, limits inclusive;
the radicals $R^2$, $R^3$ and $R^4$, which may be identical or different, represent hydrogen or optionally functionalized, aliphatic, cycloaliphatic or cyclic, saturated or unsaturated monovalent hydrocarbon-based radicals containing from 1 to 30 carbon atoms and preferably from 1 to 22 carbon atoms, limits inclusive;

r is 0 or 1;
q is an integer from 0 to 2;
p is 0 or 1,
with the proviso that:
when p=1, then r is 0 and when p=0, then q=0 and r=1.

Examples of saturated aliphatic hydrocarbon-based radicals that may especially be mentioned include linear or branched, substituted or unsubstituted $C_1$-$C_{30}$ and preferably $C_1$-$C_{22}$ alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Examples of saturated cyclic hydrocarbon-based radicals that may especially be mentioned include cyclopentyl and cyclohexyl radicals, which are optionally substituted, in particular with alkyl radicals.

Examples of unsaturated aliphatic hydrocarbon-based radicals that may especially be mentioned include linear or branched, substituted or unsubstituted, $C_2$-$C_{30}$ and preferably $C_2$-$C_{22}$ alkenyl or alkynyl radicals, and in particular vinyl, allyl, oleyl and linoleyl radicals.

Examples of unsaturated cyclic hydrocarbon-based radicals that may especially be mentioned in particular include aryl radicals such as phenyl and naphthyl, which are optionally substituted, in particular with alkyls, for instance a tolyl radical, and examples of unsaturated cycloaliphatic radicals that may be mentioned more particularly include benzyl and phenylethyl radicals.

The term "functionalized radicals" more particularly means radicals comprising in their chemical structure, either in the main chain or on a secondary chain unit, one or more functional groups especially such as esters, ethers, alcohols, amines, amides and ketones, but preferably esters.

The preferred amide-based oils of formula (III) are chosen from those in which:

$R^1$ represents a linear or branched $C_1$-$C_{22}$ alkyl radical; a linear or branched $C_2$-$C_{22}$ alkenyl radical; an aryl radical;

$R^2$ represents a hydrogen atom or a linear or branched $C_1$-$C_6$ alkyl group;

$R^3$ represents a hydrogen atom or a linear or branched $C_1$-$C_6$ alkyl group;

$R^4$ represents a linear or branched $C_1$-$C_{10}$ alkyl radical or a linear or branched $C_2$-$C_{10}$ alkenyl radical or a sterol residue.

In formula (III) presented above, the group $R^1$(CO)— is an acyl group of an acid preferably chosen from the group formed by acetic acid, toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These acids may also contain a hydroxyl group.

In formula (III), when p is 1, the portion —N($R^2$)CH($R^3$)($CH_2$)q(CO)— of the amino acid ester is preferably chosen from those corresponding to the following amino acids:

glycine, alanine, valine, leucine, isoleucine, serine, threonine, proline, hydroxyproline, β-alanine, N-butyl-β-alanine, aminobutyric acid, aminocaproic acid, sarcosine or N-methyl-β-alanine.

In formula (III), when p is 1, the portion of the amino acid esters corresponding to the group $OR^4$ may be obtained from alcohols chosen from the group formed by methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

The oils containing in their structure at least one amide function of formula (III) in accordance with the invention are known per se. Some of them are especially described with their methods of preparation in patent applications EP 1 044 676 and EP 0 928 608 from the company Ajinomoto Co. Others are known in cosmetics, for instance insect repellents such as ethyl N-acetyl-N-butylaminopropionate or N,N-diethyltoluamide.

Among the compounds of formula (III) that are particularly preferred, mention may be made of:

(1) ethyl N-acetyl-N-butylaminopropionate, having the following formula:

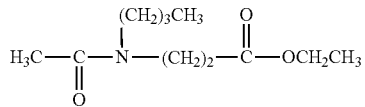

such as the product sold under the trade name Repellent R3535 by the company Merck;

(2) isopropyl N-lauroylsarcosinate of formula:

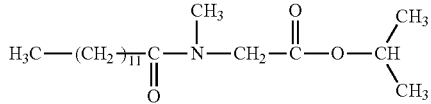

such as the product sold under the name Eldew® SL-205 by the company Ajinomoto;

(3) N,N-diethyltoluamide of formula:

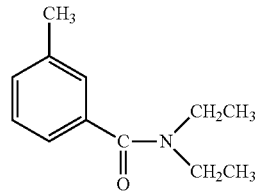

such as the product sold under the trade name Deet by the company Showa Denko.

The oil(s) containing in their structure at least one amide function as defined above is (are) present in the compositions according to the invention are in concentrations preferably ranging from 0.1% to 24% by weight, preferably from 0.5% to 20% by weight, more preferably from 0.5% to 10% by weight, relative to the total weight of the composition.

Crosslinked Copolymer(s)

The composition of the present invention comprises at least one crosslinked copolymer comprising at least one unit of an unsaturated olefinic carboxylic acid and at least one unit of a ($C_{10}$-$C_{30}$)alkyl ester of unsaturated carboxylic acid.

In particular, the unsaturated olefinic carboxylic acid unit is a hydrophilic unit.

In particular, the $(C_{10}-C_{30})$alkyl ester of unsaturated carboxylic acid unit is a hydrophobic unit.

Thus, such crosslinked copolymer may comprise at least one hydrophilic unit of the olefinic unsaturated carboxylic acid type and at least one hydrophobic unit of $(C_{10}-C_{30})$alkyl ester of unsaturated carboxylic acid type.

As used herein, "at least one crosslinked copolymer" means one crosslinked copolymer or a mixture of copolymers.

In one embodiment, said copolymer is a block copolymer.

As used herein, the term $(C_{10}-C_{30})$alkyl means an alkyl group, linear or branched, comprising from 10 to 30 carbon atoms.

Accordingly, $(C_{10}-C_{30})$alkyl esters of unsaturated carboxylic acids in accordance with the invention include for example lauryl acrylate, stearyl acrylate, decyl acrylate, isodecyl acrylate, dodecyl acrylate, lauryl methacrylate, stearyl methacrylate, decyl methacrylate, isodecyl methacrylate, and dodecyl methacrylate.

In one embodiment, the molecular weight of the above-mentioned copolymer is of at least 50 kD.

In one embodiment, the above-mentioned crosslinked copolymer are chosen from those comprising:
  at least one unit derived from olefinic unsaturated carboxylic acid monomers of formula (IV):

$$H_2C=\underset{R_1}{\overset{}{C}}-\underset{O}{\overset{\parallel}{C}}-OH \qquad \text{IV}$$

wherein $R_1$ is selected from the group consisting of H, $CH_3$, and $C_2H_5$, (which corresponds respectively to acrylic acid, methacrylic acid and ethacrylic acid units), and
  at least one unit derived from $(C_{10}-C_{30})$alkyl esters of unsaturated carboxylic acid monomers of formula (V):

$$H_2C=\underset{R_2}{\overset{}{C}}-\underset{O}{\overset{\parallel}{C}}-OR_3 \qquad \text{V}$$

wherein $R_2$ is selected from the group consisting of H, $CH_3$, and $C_2H_5$ (which corresponds respectively to acrylate, methacrylate and ethacrylate units), and $R_3$ is a saturated or unsaturated, branched or unbranched $(C_{10}-C_{30})$alkyl group.

As used herein, the term "at least one unit derived from olefinic unsaturated carboxylic acid monomers of formula (IV)" means that said unit is formed from the monomers of formula (IV), for example by polymerization of the monomers of formula (IV).

In one embodiment, for example, $R_2$ is chosen from H (acrylate units) and $CH_3$ (methacrylate units) and $R_3$ is chosen from $(C_{12}-C_{22})$alkyl groups.

Crosslinked copolymer of this type are for example described and prepared according to U.S. Pat. Nos. 3,915,921 and 4,509,949, the disclosures of which are incorporated by reference herein.

In one embodiment, the crosslinked copolymer that can be used include those formed from a mixture of monomers comprising:
  (a) acrylic acid,
  (b) at least one ester of formula (V) described above wherein $R_2$ is chosen from H and $CH_3$, and $R_3$ is chosen from alkyl groups comprising from 12 to 22 carbon atoms, and
  (c) at least one crosslinking agent chosen from copolymerizable polyethylenic unsaturated monomers such as diallyl phthalate, allyl (meth)acrylate, divinylbenzene, (poly)ethylene glycol dimethacrylate and methylenebisacrylamide.

In one embodiment, the crosslinked copolymers of the invention that can be used include (% being given with respect to the total weight of the respective copolymers):
  copolymers comprising from 95% to 60% by weight of acrylic acid (hydrophilic unit), from 4% to 40% by weight of $C_{10}-C_{30}$ alkyl acrylate (hydrophobic unit), and from 0.1% to 6% by weight of crosslinking polymerizable monomer, and
  copolymers comprising from 98% to 96% by weight of acrylic acid (hydrophilic unit), from 1% to 4% by weight of $C_{10}-C_{30}$ alkyl acrylate (hydrophobic unit) and from 0.1% to 0.6% by weight of crosslinking polymerizable monomer such as those described above.

Among the above crosslinked copolymers, the products sold by the company Lubrizol under the trade names PEMULEN TR1®, PEMULEN TR2®, and CARBOPOL 1382® can be used.

Preferably, the crosslinked copolymer used in the present invention is PEMULEN TR2®, which is a acrylates/$C_{10}-C_{30}$ alkyl acrylate crosspolymer, with a viscosity of 1050 to 3750 cps measured by Brookfield RV at 25° C. in aqueous solution at 0.2% w/v, S4, 20 rpm.

In one embodiment, the composition of the invention comprises from 0.05% to 5% by weight, preferably from 0.1% to 1% by weight, more preferably from 0.1% to 0.5% by weight of above-mentioned crosslinked copolymer, based on the total weight of the composition.

The composition of the present invention comprises water in an amount greater than or equal to 75% by weight, relative to the total weight of the composition.

Preferably the composition of the present invention comprises water in an amount from 80% to 95% by weight, relative to the total weight of the composition.

According to an embodiment, the present invention relates to a composition for caring for and/or making up keratin materials, comprising, relative to the total weight of the composition:
  (a) greater than or equal to 75% by weight of water;
  (b) from 0.01% to 3% by weight of at least one hydroxylated diphenylmethane derivative of the formula (II), (II)

[Chemical structure of hydroxylated diphenylmethane derivative with two phenyl rings connected by a CH(CH3) group, with OH groups on both rings]

(c) from 0.5% to 20% by weight of at least one oil selected from the group consisting of ethyl N-butylaminopropionate, isopropyl N-lauroylsarcosinate, N,N-diethyltoluamide, or a mixture thereof; and
  (d) from 0.1% to 1% by weight of at least one crosslinked copolymer comprising at least one unit of an unsaturated olefinic carboxylic acid and at least one unit of a $(C_{10}-C_{30})$alkyl ester of unsaturated carboxylic acid.

Aqueous Phase

According to an embodiment, the composition of the invention comprises at least one aqueous phase.

Preferably the aqueous phase is a continuous aqueous phase.

According to an embodiment, the aqueous phase includes, in addition to water, water-soluble additives and/or solvents.

The aqueous phase may also comprise organic solvents miscible with water (at room temperature 25° C.) such as for example monoalcohols having from 2 to 6 carbon atoms such as ethanol, isopropanol; polyols notably having from 2 to 20 carbon atoms, preferably from 2 to 10 carbon atoms, and preferentially having from 2 to 6 carbon atoms, such as glycerol, propylene glycol, butylene glycol, pentylene glycol, hexylene glycol, caprylylglycol, dipropylene glycol, diethylene glycol; glycol ethers (notably having from 3 to 16 carbon atoms) such as mono-, di- or tri-propylene glycol ($C_1$-$C_4$)alkyl ethers, mono-, di- or tri-ethylene glycol ($C_1$-$C_4$) alkyl ethers and mixtures thereof.

According to an embodiment, the aqueous phase of the compositions of the invention comprises a polyol notably glycerol, caprylylglycol or propylene glycol, and a monoalcohol, notably ethanol.

The amount of aqueous phase may range, for example, from 0.1% to 99.9% by weight, preferably from 0.5% to 99% by weight relative to the total weight of the composition.

The aqueous phase may also contain other additives such as water-soluble active ingredients, preservatives, salts, gelling agents, fillers, additional water-soluble or water-dispersible polymers, water-soluble dyes, and so on.

Oily Phase

According to an embodiment, the composition according to this invention further comprises at least one oily phase.

Preferably, the oily phase is dispersed oily phase.

The oily phase may further comprise, in addition to the oil (b) as disclosed above, additional oil(s).

The term "oil" refers to any fatty body in liquid form at room temperature (20-25° C.) and atmospheric pressure. These oils may be of animal, plant, mineral or synthetic origin.

The oils may be volatile or non-volatile.

The term "volatile oil" refers to any non-aqueous medium capable of evaporating from the skin or lips, in less than one hour, at room temperature (20-25° C.) and atmospheric pressure (760 mmHg). The volatile oil is a volatile cosmetic oil, liquid at room temperature. More specifically, a volatile oil has an evaporation rate of between 0.01 and 200 mg/cm$^2$/min, inclusive.

The term "non-volatile oil" is intended to mean an oil remaining on the skin or lips at ambient temperature and atmospheric pressure. More specifically, a non-volatile oil has an evaporation rate strictly below 0.01 mg/cm$^2$/min.

To measure this evaporation rate, 15 g of oil or a mixture of oils to be tested are introduced into a crystallizer, 7 cm in diameter, placed on a scale located in a large 0.3 m$^3$ chamber temperature-controlled at a temperature of 25° C., and humidity-controlled with a relative humidity of 50%. The liquid is left to evaporate freely, without stirring, by providing ventilation with a fan (PAPST-MOTOREN, reference 8550 N, rotating at 2700 rpm) positioned vertically above the crystallizer containing the solvent, with the blades directed toward the crystallizer and at a distance of 20 cm from the base of the crystallizer. The mass of oil remaining in the crystallizer is measured at regular intervals. The evaporation rates are expressed in mg of oil evaporated per surface area unit (cm$^2$) and per time unit (minute).

The oils that are suitable for the present invention may be hydrocarbon-based, silicone-based or fluorine-based.

According to the invention, the term "silicone oil" refers to an oil including at least one silicon atom, and in particular at least on Si—O group.

The term "fluorine oil" refers to an oil including at least one fluorine atom.

The term "hydrocarbon oil" refers to an oil containing primarily hydrogen and carbon atoms.

The oils may optionally include oxygen, nitrogen, sulfur and/or phosphorus atoms, for example, in the form of hydroxyl or acid radicals.

Preferably, the oily phase is present in an amount of less than 25% by weight, preferably from 0.1% to 20% by weight, more preferably from 0.5% to 10% by weight, relative to the total weight of the composition.

Galenic Form

The composition of the present invention is preferably in the form of an emulsion or dispersion.

More particularly, the composition according to the invention is in the form of an oil in water emulsion, or an oil in water dispersion.

Viscosity

According to a preferred embodiment, the composition of the present invention has a viscosity of from 10 UD (Deviation Units) to 80 UD, preferably from 10 UD to 50 UD, measured at 25° C. using a Rheomat 180 viscometer equipped with a spindle M2 rotating at 200 rpm.

As described above, the viscosity of the composition according to the invention is measured at 25° C., using a ProRheo R180 viscometer equipped with a spindle M2 rotating at 200 rpm from the company ProRheo.

Adjuvants

In a known manner, the composition of the invention may also contain adjuvants that are common in cosmetics and/or dermatology, such as preserving agents, antioxidants, complexing agents, pH modifiers (acidic or basic), fragrances, fillers, bactericides, odour absorbers, film-forming polymers, surfactants such as anionic, amphoteric, cationic, or nonionic surfactants.

Needless to say, a person skilled in the art will take care to select this or these optional additional compound(s), and/or the amount thereof, such that the properties of the composition according to the invention are not, or are not substantially, adversely affected by the envisaged addition.

Method and Use

According to one embodiment the composition of the present invention is prepared as follows:

mixing the ingredient (b) and (c) as described above to obtain an oily phase by stirring until homogeneous;

mixing water and the mixture obtained above by stirring until homogeneous;

mixing the ingredient (d) as described above with the mixture obtained in the preceding step by stirring;

homogenizing the mixture obtained in the previous step at 1500-5000 rpm for 10 minutes.

Lab Homogenization is preferably performed with a high shear mixer, such as those manufactured by Silverson.

Stirring is preferably performed by VMI mixers.

The composition of the present invention is advantageously used to prepare a cosmetic water.

Advantageously, the composition of the present invention is a cosmetic composition for caring for and/or making up keratin materials, and may be in form of lotion, toner, water, or spray. In particular, the composition of the present invention is a cosmetic toner or water for caring for keratin materials, in particular the skin.

The composition of the present invention can be used for a cosmetic process, such as a cosmetic process or method, for making up/caring for the keratin materials, such as the skin, in particular the face and the lips, by being applied to the skin, especially the face.

The present invention also relates to a use of the composition according to the present invention, for making up/caring for the skin, especially for the skin, and in particular the face.

The present invention relates to a cosmetic process for caring for and/or making up keratin materials, comprising the application, to the surface of the said keratin material, of at least one composition of the invention, wherein the keratin material is preferably skin, in particular face.

The present invention relates to a cosmetic process for hydrating of a keratin material, comprising the application, to the surface of the keratin material, of at least one composition as defined according to the invention.

The examples that follow are aimed at illustrating the compositions and processes according to this invention, but are not in any way a limitation of the scope of the invention.

EXAMPLES

Example 1 Preparation of Invention and Comparative Formulas

Formulas according to the invention and outside of the invention (comparative) were prepared according to the concentration given in table 1.

TABLE 1

| | | Invention formula 1, 2, and Comparative formula 1' | | |
|---|---|---|---|---|
| | | % by weight, by active ingredient | | |
| | | Invention formula | | Comparative formula |
| Phase | INCI name | 1 | 2 | 1' |
| A | WATER | Qs 100 | Qs 100 | Qs 100 |
| A | GLYCERIN | 5.00 | 5.00 | 5.00 |
| A | BUTYLENE GLYCOL | 8.00 | 8.00 | 8.00 |
| A | PRESERVATIVE | 0.60 | 0.60 | 0.60 |
| B | ISOPROPYL LAUROYL SARCOSINATE (Eldew ® SL-205 from Ajinomoto) | 0.75 | 2.5 | 0.75 |
| B | PHENYLETHYL RESORCINOL (Symwhite ® 377 from Symrise) | 0.30 | 0.30 | 0.30 |
| B | ACRYLATES/C10-30 ALKYL ACRYLATE CROSSPOLYMER (PEMULEN ™ from Goodrich) | 0.30 | 0.30 | 0 |
| C | AMMONIUM POLYACRYLOYLDIMETHYL TAURATE | 0.40 | 0.40 | 0.40 |
| C | CARBOMER (Carbopol ® 981 polymer from Lubrizol) | 0 | 0 | 0.3 |
| D | SODIUM HYDROXIDE | 0.08 | 0.08 | 0.08 |
| D | WATER | 3.00 | 3.00 | 3.00 |

The comparative formula 1' contains polymer Carbomer which is outside the scope of the invention.

The Invention and Comparative formulas were prepared following the steps of:
1. at 75° C., solubilizing phase A using homogenizer;
2. solubilizing phenylethyl resorcinol in phase B at room temperature (25° C.) by stirring;
3. introducing phase B into phase A, decreasing the temperature of the mixture and stirring the mixture;
4. at 60° C., introducing C into mixture A+B and stirring until a homogenous mixture was obtained keep decreasing temperature at the same time;
5. at 30° C., slowing down stirring and adding phase D under stirring.

Comparative formula A, lamellar phase emulsion with phenylethyl resorcinol, was prepared, wherein contains a known agent for improving the solubility and stability of phenylethyl resorcinol, dicaprylyl carbonate:

| Phase | INCI name | % by weight by active ingredient |
|---|---|---|
| A | WATER | QS100 |
| A | GLYCERIN | 7.00 |
| A | BUTYLENE GLYCOL | 7.00 |
| A | PRESERVATIVE | 0.60 |
| B | CARBOMER (Carbopol ® 981 polymer from Lubrizol) | 0.20 |
| F | ALCOHOL | 5.00 |
| C | SODIUM HYDROXIDE | 0.02 |

-continued

| Phase | INCI name | % by weight by active ingredient |
|---|---|---|
| D | SODIUM METHYL STEAROYL TAURATE (NIKKOL SMT from Nikko) | 1.00 |
| E | PHENYLETHYL RESORCINOL (Symwhite ® 377 from Symrise) | 0.30 |
| E | CETEARYL ALCOHOL (Lanette ® O OR from BASF) | 0.8 |
| E | DICAPRYLYL CARBONATE (Cetiol ® CC from BASF) | 1.20 |

The comparative formula A was prepared following the steps of:
1. melting phase D and phase E, respectively, in a melter at the temperature of 75-80° C. with stirring at 500-1000 rpm/min until a homogeneous phase;
2. adding phase E to phase D, using mixer at 2000-2500 rpm (silverson) for 10 minutes to obtain a homogenous mixture;
3. stirring the mixture using VMI apparatus at a speed of 500 rpm/min, whiling gradually cooling down the mixture to room temperature at a speed of 1° C./minute;
4. melting phase A in a melter at the temperature of 90° C. with stirring at 500-1000 rpm/min until a homogeneous phase, and cooling down phase A to 60° C.;
5. adding phase B to phase A, while stirring using VMI at 800-1000 rpm/min for 10 minutes, leaving the mixture 1 hour for dispersion;
6. diluting phase C with water, and adding the diluted phase C to the mixture obtained above;
7. adding the mixture obtained in step 3 to the mixture obtained in step 6, stirring at 500 rpm/min until homogeneous.

Example 2: Evaluation of the Invention and Comparative Formulas

The viscosity, stability and bioavailability of the Invention and/or Comparative formulas were evaluated.

The stability of the formulas were evaluated by leaving the formulas at 4° C., 40° C., and 45° C. for 2 months, and a cycle from −20° C. to 20° C./24 hours for 10 days, and observing the formulas using microscope under polarized light.

The bioavailability was evaluated by the protocol from the company Biogalenys. In particular, the protocol is as follow:

whole frozen human skin obtained from abdominal plastic surgery was used in this study. Each skin sample had an application area of 2 cm² after assembly on static Franz-type diffusion cell. 5 mg/cm² of each invention and comparative formulas were applied onto the skin surface for 16 hours. Three different donors with 3 samples per donor were used. Thus, 9 results were generated on one formula.

After 16 hours of exposure time, skin surface was washed with a solution containing 5% of sodium lauryl ether sulfate (used as cleanser), then rinsed with water, and at last dried with cotton swab.

The cutaneous distribution profile of phenylethyl resorcinol was determined by LC/MSMS analysis in the different compartments (skin excess, stratum corneum, epidermis, dermis and receptor fluid). LC/MSMS analysis was chosen for its great sensibility and specificity.

The bioavailability is calculated and represented by the following equation:

Bioavailability of phenylethyl resorcinol (% by weight)=Amount of phenylethyl resorcinol in the skin compartments/total amount of phenylethyl resorcinol applied on the skin×100%

The higher the number is, the better bioavailability of the formula is. For the purpose of the present invention, a bioavailability of greater than or equal to 10% is pursued, which is considered as an improved efficacy comparing to the prior art.

The results of the evaluation are as follow:

| | Invention formula | | Comparative formula | |
|---|---|---|---|---|
| Item | 1 | 2 | 1' | A |
| Viscosity | 14 | 14 | N/A (not stable) | 21 |
| Stability | Stable | Stable | Unstable, phase separation after 2 months storage | Stable |
| Bioavailability (% by weight) | 18 | 15 | Not available, formula unstable | 7 |

It is observed that invention formulas 1 and 2, as well as the comparative formula A all have a desired low viscosity, which provide a light, fresh, and hydration feeling to the skin. Whereas the comparative formula 1' is not stable.

The invention formulas 1 and 2, as well as comparative formula A are stable over 2 months, with no change both in terms of macro- or micro-appearance. Whereas the comparative formula 1' is not stable after 2 months.

Moreover, comparing to the comparative formula A (contains dicaprylyl carbonate, an known agent for improving the stability and solubility of phenylethyl resorcinol, and therefore improving the bioavailability), the invention formulas 1 and 2 represent an improved bioavailability (greater than 10%), and met the purpose of the present invention.

The invention claimed is:
1. A composition comprising:
(a) at least 82.8% by weight of water, relative to a total weight of the composition;
(b) at least one hydroxylated diphenylmethane derivative of the formula (I),

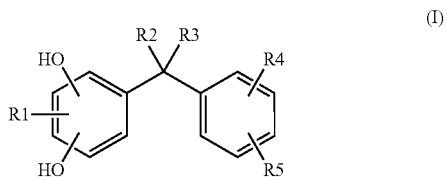

wherein R1 is a hydrogen atom or a methyl group, R2 is a hydrogen atom or a methyl group, R3 is a methyl group,
R4 and R5 are, each independently a hydrogen atom or a methyl group;
(c) at least one oil selected from the group consisting of ethyl N-butylaminopropionate, isopropyl N-lauroylsarcosinate, N,N-diethyltoluamide, and mixtures thereof; and
(d) ACRYLATES/C10-30 ALKYL ACRYLATE CROSSPOLYMER
wherein
a viscosity of the ACRYLATES/C10-30 ALKYL ACRYLATE CROSSPOLYMER is from 1050 to 3750 cps at 25° C. in aqueous solution at 0.2% w/V,
a bioavailability of the at least one hydroxylated diphenylmethane derivative of the formula (I) is equal to or greater than 10%, and
the composition is in a form of an oil in water emulsion, or an oil in water dispersion.

2. The composition of claim 1, wherein the hydroxylated diphenylmethane derivative of formula (I) is a compound of formula (II):

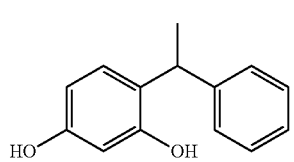

(II)

3. The composition of claim 1, wherein the hydroxylated diphenylmethane derivative of formula (I) is present in an amount ranging from 0.005% to 5% by weight, relative to the total weight of the composition.

4. The composition according to claim 1, wherein the oil (c) is isopropyl N-lauroylsarcosinate.

5. The composition according to claim 1, wherein the oil c) is present in an amount ranging from 0.1% to 24% by weight, relative to the total weight of the composition.

6. The composition according to claim 1, wherein the ACRYLATES/C10-30 ALKYL ACRYLATE CROSSPOLYMER is selected from the group consisting of:
copolymers comprising from 95% to 60% by weight of acrylic acid, from 4% to 40% by weight of $C_{10}$-$C_{30}$ alkyl acrylate, and from 0.1% to 6% by weight of crosslinking polymerizable monomer, based on a total weight of the copolymer; and
copolymers comprising from 98% to 96% by weight of acrylic acid, from 1% to 4% by weight of $C_{10}$-$C_{30}$ alkyl acrylate, and from 0.1% to 0.6% by weight of crosslinking polymerizable monomer, based on the total weight of the copolymer.

7. The composition according to claim 1, wherein the ACRYLATES/C10-30 ALKYL ACRYLATE CROSSPOLYMER is present in an amount ranging from 0.05% to 5% by weight, relative to the total weight of the composition.

8. The composition according to claim 1, wherein a viscosity of the composition ranges from 10 UD (Deviation Units) to 80 UD, measured at 25° ° C. using a Rheomat 180 viscometer equipped with a spindle M2 rotating at 200 rpm.

9. A composition for caring for and/or making up keratin materials, comprising the composition of claim 1.

10. A composition for caring for and/or making up keratin materials, comprising, relative to a total weight of the composition:
(a) at least 82.8% by weight of water;
(b) from 0.01% to 3% by weight of at least one hydroxylated diphenylmethane derivative of the formula (II),

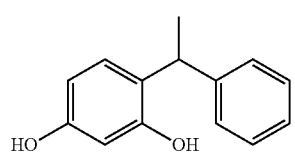

(II)

(c) from 0.5% to 20% by weight of isopropyl N-lauroylsarcosinate; and
(d) ACRYLATES/C10-30 ALKYL ACRYLATE CROSSPOLYMER wherein
a viscosity of the ACRYLATES/C10-30 ALKYL ACRYLATE CROSSPOLYMER is from 1050 to 3750 cps at 25° C. in aqueous solution at 0.2% w/v,
a bioavailability of the at least one hydroxylated diphenylmethane derivative of the formula (I) is equal to or greater than 10%, and
the composition is in a form of an oil in water emulsion, or an oil in water dispersion.

11. A cosmetic process for caring for and/or making up keratin materials, comprising applying to a surface of the keratin material the composition according to claim 1.

12. The cosmetic process according to claim 11, wherein the surface of a keratin material is a face.

* * * * *